United States Patent [19]

Takaishi et al.

[11] 3,976,707

[45] Aug. 24, 1976

[54] PROCESS FOR THE PREPARATION OF TRICYCLO [5.3.1.0$^{3,8}$] UNDECANE

[75] Inventors: Naotake Takaishi, Iwademachi; Yoshiaki Inamoto, Wakayama; Kiyoshi Tsuchihashi, Kainan, all of Japan

[73] Assignee: Kao Soap Co., Ltd., Tokyo, Japan

[22] Filed: Apr. 28, 1975

[21] Appl. No.: 572,464

[30] Foreign Application Priority Data

May 8, 1974 Japan.................................. 49-50815

[52] U.S. Cl. ...................... 260/666 PY; 260/666 M
[51] Int. Cl.$^2$.......................................... C07C 13/54
[58] Field of Search .................. 260/666 PY, 666 M

[56] References Cited
OTHER PUBLICATIONS

Krautz et al., Chem. Commun. 1971, 1287.

Krautz et al., J. Amer. Chem. Soc. 95, 5662, 1973.

Schleyer et al., *Chem. Letters*, 1189, 1973.

N. S. Vorobeva, O. A. Arefeu, V. I. Epshev, and A. A. Petrov, Chem. Ab. 75: 19562e [Neftekimiya, 11, 163, 1971].

Naotake Takaishi et al., J. Org. Chem. 40, No. 3, pp. 276–281, 1975.

Majerski et al., Tehrahedron Letters, 4915, 1973.

*Primary Examiner*—Veronica O'Keefe
*Attorney, Agent, or Firm*—Woodhams, Blanchard and Flynn

[57] ABSTRACT

A process for the preparation of tricyclo [5.3.1.0$^{3,8}$]-undecane, in which endo-tetramethylenenorbornane is isomerized in the presence of an acid catalyst.

6 Claims, No Drawings

PROCESS FOR THE PREPARATION OF TRICYCLO [5.3.1.0$^{3,8}$] UNDECANE

BACKGROUND OF THE INVENTION

1. FIELD OF THE INVENTION

This invention relates to a process for the preparation of tricyclo[5.3.1.0$^{3,8}$]undecane. More particularly, this invention relates to a process for preparing tricyclo[5.3.1.0$^{3,8}$]-undecane (II), which is a tricyclic hydrocarbon, by isomerizing endo-tetramethylenenorbornane (I) according to the following reaction scheme (1):

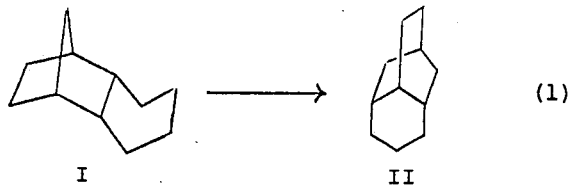

Reactions capable of forming tricyclo[5.3.1.0$^{3,8}$]undecane (II) are known in the art (for example, Krantz et al, Chem. Commun., 1287 (1971), J. Am. Chem. Soc., 95, 5662 (1973); Majerski et al, Tetrahedron Letters, 4915 (1973); and Schleyer et al, Chemistry Letters, 1189 (1973)).

We previously proposed a novel synthesis process for preparing tricyclo[5.3.1.0$^{3,8}$]undecane (II) by catalytic isomerization of exo-tetramethylenenorbornane (III) in the presence of an acid catalyst (Japanese Patent Application No. 77621/73 (U.S. Patent Application No. 485 068 now U.S. Pat. No. 3,894,100); and Chemistry Letters, 1185 (1973)).

2. SUMMARY OF THE INVENTION

We have discovered an improved process for synthesizing tricyclo[5.3.1.0$^{3,8}$]undecane (II). Our process possesses unexpected advantages in comparison with the prior processes.

More specifically, we have discovered that endo-tetramethylenenorbornane (I), which is a steric isomer of exotetramethylenenorbornane (III), can be isomerized to tricyclo[5.3.1.0$^{3,8}$]undecane (II) using an unexpectedly lesser amount of catalyst, namely, an amount corresponding to ½ to 1/10 of the amount of the catalyst needed for isomerization of exo-tetramethylenenorbornane (III), and that the reaction time can be greatly shortened. In accordance with this invention, there is provided a process in which tricyclo[5.3.1.0$^{3,8}$] undecane (II) can be prepared using a smaller amount of a catalyst than is employed in the prior processes.

It is well known that exo- and endo-isomers of tetramethylenenorbornane are in thermodynamic equilibrium as shown below, in the presence of an acid catalyst or certain metal catalysts (McKervey et al, J. Am. Chem. Soc., 92, 2922 (1970)):

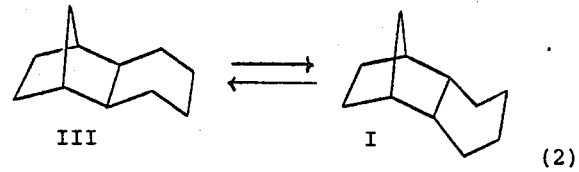

In the catalytic isomerization of exo-tetramethylenenorbornane (III) to tricyclo[5.3.1.0$^{3,8}$]undecane (II) in the presence of an acid catalyst (Japanese Patent Application No. 77621/73, corresponding to U.S. Ser. No. 485 068 now U.S. Patent No. 3,894,100), although the exo-endo equilibrium conditions are satisfied, endotetramethylenenorbornane (I), as a reaction intermediate, is not detected at all. As a result of a detailed examination of the catalytic isomerization of endo-tetramethylenenorbornane (III) in the presence of an acid catalyst, we found that endotetramethylenenorbornane (I) is isomerized to tricyclo-[5.3.1.0$^{3,8}$] undecane (II) at a reaction rate about 4,000 times as high as the isomerization rate of exo-tetramethylenenorbornane (III).

Accordingly, it is believed that the reason why no endo-isomer (I) is detected in the isomerization of the exo-isomer (III) to tricyclo[5.3.1.0$^{3,8}$]undecane (II) is that even if the endo-isomer (I) were to be formed by the equilibrium with the exo-isomer (III), it will be consumed at a rate about 4000 times higher than the consumption rate of the exo-ismer (III).

Based on the foregoing findings, this invention provides a process for preparing tricyclo[5.3.1.0$^{3,8}$]undecane (II) in a very short time by isomerizing endo-tetramethylenenorbornane (I) in the presence of a small amount of an acid catalyst.

As regards the catalytic isomerization of endo-tetramethylenenorbornane (I) to 1-methyladamantane in the presence of an acid catalyst, Whitting et al (J. Chem. Soc., Perkin I, 2644 (1972)) report that the isomerization rate thereof is quite the same as the isomerization rate of exo-tetramethylenenorbornane, and the presence of tricyclo[5.3.1.0$^{3,8}$]undecane (I) was not detected in this reaction.

As a result of detailed examination of the catalytic isomerization of endo-tetramethylenenorbornane in the presence of an acid catalyst, we found that about midway in the isomerization reaction thereof to 1-methyladamantane, endotetramethylenenorbornane (I) disappears and a mixture of several intermediates, including tricyclo[5.3.1.0$^{3,8}$]undecane (II), is formed, and this intermediate reaction mixture is then isomerized to 1-methyladamantane. It was also found that in the catalytic isomerization of endo-tetramethylenenorbornane (I) in the presence of an acid catalyst, if the reaction is stopped at an appropriate time (approximately midway), or if the reaction is carried out under milder conditions than those adopted for the synthesis of 1-methyladamantane, an intermediate mixture containing a substantial amount of tricyclo[5.3.1.0$^{3,8}$]undecane (II) is obtained. When the thus-obtained mixture is separated by appropriate means such as distillation and chromatography, tricyclo[5.3.1.0$^{3,8}$]-undecane (II) can be obtained in a high yield such as 65 percent.

When the intended product of this invention, namely tricyclo[5.3.1.0$^{3,8}$]undecane (II) is further reacted, it is converted to 1-methyladamantane. From this fact it will readily be understood that the use of the endo-isomer (I) as the starting substance in the process of this invention is advantageous in comparison with the use of exo-tetramethylenenorbornane (III). More specifically, because each of the conditions of (1) the use of a large quantity of catalyst and (2) a long reaction time, promotes further conversion of the intended product (II) of this invention to 1-methyladamantane, under such reaction conditions the yield of the intended product (II) is reduced. In this point, the use of the endo-isomer (I) as the starting substance is advantageous for improving the yield of the intended product (II), because the reaction is completed in a short time using a small amount of a catalyst. In fact, when the exo-isomer (III) is used as the starting substance, the yield is at most about 50 percent (Japanese Laid-Open Patent Application No. 77621/73), whereas in the process of this invention the yield of tricyclo[5.3.1.0$^{3,8}$]undecane (II) can be improved to about 65 percent.

As is apparent from the foregoing discussion, the process of this invention is characterized in that endo-tetramethylenenorbornane (I) is isomerized under limited, mild conditions. When endo-tetramethylenenorbornane (I) is isomerized under severe conditions, the reaction advances in a very short time to the stage of formation of 1-methyladamantane and it is difficult to isolate a mixture of tricyclic undecanes including the desired intermediate product (II). The term "isomerization under severe conditions" refers to an isomerization reaction which is conducted generally in the absence of a solvent at a temperature of about 50°C. or higher, by using such a strong Lewis acid catalyst as aluminum halides (chlorides or bromides) and antimony pentahalides (chlorides or bromides) in an amount of more than 50 mole percent based on the starting substance (I). The term "isomerization under limited, mild conditions" employed in this invention for forming large quantities of intermediates including the intended product (II), means an isomerization reaction which is conducted in the presence of a solvent at a temperature of up to about 60°C. by using as a catalyst a Brønsted acid or up to about 10 mole percent of a Lewis acid, while the amount formed of the intended product (II) is measured by, for example, gas chromatography. The reaction is brought to an end when the concentration of the intended product (II) reaches the highest level in the reaction mixture.

Various acid catalysts are preferably employed for attaining such mild conditions. When a Brønsted acid, such as fluorosulfonic acid and trifluoromethanesulfonic acid, is used as the acid catalyst, good results can be obtained when such acid catalyst is used in an amount of from 0.1 to 10 moles, preferably about one mole, per mole of the starting substance (I). When an aluminum halide is used as the catalyst, the objects of this invention can be sufficiently attained when such catalyst is used in an amount of 0.001 to 0.1 mole, preferably 0.01 to 0.05 mole, per mole of the starting substance (I). If an aluminum halide catalyst is used in a larger amount, isomerization of the intended product (II) to 1-methyladamantane is caused to advance simultaneously. Therefore, the use of the aluminum halide catalyst in a larger amount is not satisfactory.

The kind of solvent to be used for the reaction is not critical, and any of the conventional solvents of the classes or aromatic hydrocarbons, aliphatic hydrocarbons, halogenated hydrocarbons and ethers, which are inert to the catalyst, can be employed in this invention. The amount of solvent can be from 10 to 100000 weight percent, based on the weight of the starting substance (I).

The reaction can be carried out at a temperature of −30°C. to 100°C., but it is preferred that the reaction is carried out at a temperature ranging from −10°C. to 50°C. The isomerization reaction time is variable depending on the reaction temperature, catalyst and amount of catalyst. It is selected within the range of from 1 to 300 minutes, to give a maximum yield of tricyclo[5.3.1.0$^{3,8}$]undecane. The isomerization reaction is terminated when the content of tricyclo[5.3.1.0$^{3,8}$]undecane in the reaction mixture is at least about 80 weight percent.

The starting substance of this invention, namely endomethylenenorbornane (I), can be obtained by subjecting a Diels-Alder adduct (IV) of cyclopentadiene and p-benzoquinone to catalytic hydrogenation and Wolf-Kischner reduction according to the method of Whiting et al (J. Chem. Soc., Perkin I, 2644 (1972)) as represented by the following reaction scheme (2)

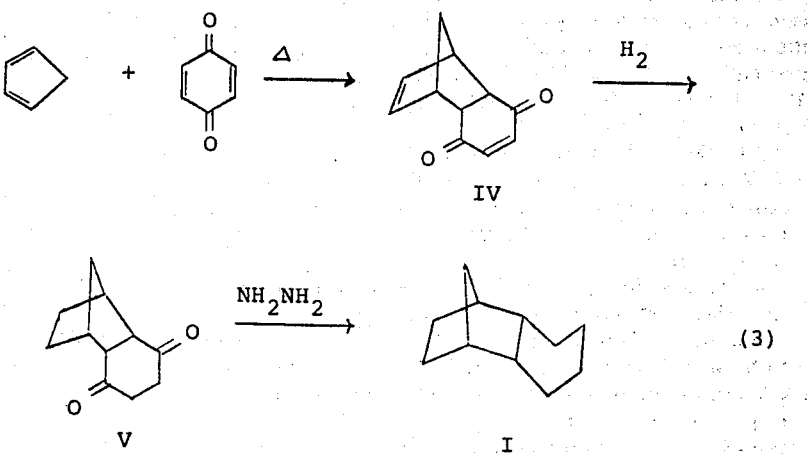

or by isomerizing a part of exo-tetramethylenenorbornane (III) to the endo-isomer (I) according to our previously proposed process using a palladium-carbon catalyst (Japanese Laid-Open Patent Application No. 78155/73) and separating the isomer (I) from the reaction mixture by an appropriate method.

Embodiments of the process of this invention will now be described in detail by reference to the following illustrative Preparations and Examples.

Preparation

A 100 ml-capacity autoclave was charged with 50 g of exo-tetramethylenenorbornane (II) and 5 g of a palladium-carbon catalyst synthesized according to the method disclosed in Japanese Laid-Open Patent Application Publication No. 78155/73), and hydrogen was introduced into the autoclave under a pressure of 5 Kg/cm². Then, the autoclave was sealed and maintained at 250°C. for 17 hours under agitation to effect the reaction. The reaction mixture was allowed to cool in ambient air (20°–25°C.) and the catalyst was separated therefrom by filtration. The filtrate was fractionated and a fraction boiling at 84° to 85°C. under 15 mm Hg was recovered to obtain 4.5 g (yield = 9%) of endo-tetramethylenenorbornane (I). Analysis results are as shown below:

$n_D^{21.5}$ = 1.5015 (the value reported by Alder et al, Ann, 627 (1959) being $n_D^{20}$ = 1.5026)

ir(cm$^{-1}$): 2915, 2850, 1480, 1460, 1312, 1288, 1158, 1124, 946, 867, 813, 774 ms(m/e) (relative intensity, %): 150 (M$^+$, 63), 135 (10), 121 (13), 109 (97), 93 (14), 82 (57), 67 (100), 55 (27)

$^1$Hnmr (CDCl$_3$ solvent): δ1.0–1.9, complex multiplet (16H), δ1.2–2.2 complex multiplet (2H)

These properties were in agreement of those of a standard product synthesized according to the method of Whiting et al according to the reaction scheme (3).

EXAMPLE 1

A solution formed by dissolving 7.5 g (0.05 mole) of endotetramethylenenorbornane (I) in 100 ml of methylene chloride was maintained at 0°C. and was agitated. Then, 4.5 g (0.03 mole) of trifluoromethanesulfonic acid was added to the solution, and the mixture was heated and refluxed under agitation for 30 minutes.

The reaction mixture was allowed to cool in ambient air (20°–25°C.) and then was placed in 100 ml of ice water. After the organic layer had been separated, the aqueous layer was extracted with methylene chloride and the methylene chloride extract was combined with the organic layer. The mixture was washed first with a saturated aqueous solution of sodium hydrogencarbonate and then with water, and then dried with anhydrous sodium sulfate. Methylene chloride was removed by distillation and a fraction boiling at 111° to 112°C. under 35 mm Hg was recovered to obtain 4.65 g (yield = 62%) of tricyclo[5.3.1.0$^{3,8}$]undecane (II). Analysis results are as shown below:

Melting point (sealed tube): 62° – 63°C.

Elemental analysis values: Found: C = 87.8%, H = 12.2% Calculated as C$_{11}$H$_{18}$: C = 87.92%, H = 12.08% ir(cm$^{-1}$): 2925, 2890, 2870, 2850, 1480, 1465, 1450, 1340, 975, 940, 895, 845 ms (m/e) (relative intensity, %): 150 (M$^+$, 100), 122 (39), 121 (39), 102 (12), 108 (16), 107 (19), 93 (27), 81 (27), 80 (46), 79 (40), 67 (35), 55 (18), 41 (40)

$^1$Hnmr (CDCl$_3$ solvent): δ1.0 – 2.0 complex multiplet $^{13}$Cnmr (CDCl$_3$ solvent, 15.1 MHz, TNS at 0 ppm) (ppm): 15.2, 24.8, 26.3, 27.1, 30.9, 31.9, 32.3, 33.1

Comparative Example 1

When exo-tetramethylenenorbornane (III) (0.05 mole) was reacted for 4 hours in the same manner as in Example 1 by using 0.05 mole (100 mole percent) of trifluoromethanesulfonic acid, 3.5 g (yield = 45%) of tricyclo[5.3.1.0$^{3,8}$]-undecane (II) was obtained.

Example 2

A solution formed by dissolving 15 g (0.1 mole) of endotetramethylenenorbornane (I) in 100 ml of methylene chloride was maintained at 0°C. and was agitated. Then, 0.65 g (0.005 mole) of anhydrous aluminum chloride was added to the solution and the mixture was heated and refluxed for 15 minutes under agitation. The reaction mixture was allowed to cool in ambient air and then was placed in ice water. After the organic layer had been separated, the aqueous layer was extracted with methylene chloride. The methylene chloride extract was combined with the organic layer, and the mixture was washed first with a saturated aqueous solution of sodium hydrogencarbonate and then with water and then dried with anhydrous sodium sulfate.

Methylene chloride was removed by distillation, and the residue was fractionated. The highest boiling point fraction (111° – 112°C. under 36 mm Hg) was recovered to obtain 7.5 g (yield = 50%) of tricyclo[5.3.1.0$^{3,8}$]undecane.

The infrared absorption spectrum, the nmr spectrum and the mass spectrum of the thus-obtained product were in agreement with those of the product (II) obtained in Example 1.

The embodiments of this invention in which an exclusive property or privilege is claimed are defined as follows:

1. A process for preparing tricyclo[5.3.1.0$^{3,8}$]undecane which comprises isomerizing endo-tetramethylenenorbornane (I), in an inert solvent, at a temperature in the range of −30°C. to 100°C., in the presence of an acid catalyst selected from the group consisting of (1) a Brønsted acid in an amount of about 0.1 to 10 moles, per mole of I and (2) a Lewis acid in an amount of 0.001 to 0.1 mole, per mole of I; terminating the isomerization reaction when the content of tricyclo[5.3.1.0$^{3,8}$]undecane in the reaction mixture is in the range of more than about 80 weight percent, excluding the solvent and the acid catalyst; and recovering tricyclo[5.3.1.0$^{3,8}$]-undecane from the reaction mixture.

2. The process according to claim 1, wherein the temperature of the isomerization reaction is in the range of −10°C. to 50°C.

3. The process according to claim 2, wherein the acid catalyst is a Bronsted acid of the group consisting of sulfuric acid, fluorosulfonic acid, chlorosulfonic acid, methanesulfonic acid, ethanesulfonic acid, trifluoromethanesulfonic acid, benzenesulfonic acid, and p-toluenesulfonic acid, and the amount of said catalyst is about 1 mole, per mole of I.

4. The method according to claim 2, wherein the acid catalyst is 0.01 to 0.05 mole of an aluminum halide or antimony pentahalide per mole of I.

5. The method according to claim 2, wherein the isomerization reaction time is from 1 to 300 minutes.

6. The method according to claim 2 including the step of monitoring the progress of the isomerization reaction and terminating the isomerization reaction when the concentration of tricyclo[5.3.1.0$^{3,8}$]undecane is a maximum in the reaction mixture.

* * * * *